United States Patent
Crook

(10) Patent No.: US 7,463,160 B2
(45) Date of Patent: Dec. 9, 2008

(54) REMOTE CONTROL OF A HYDROGEN SULFIDE GAS ALARM SYSTEM

(76) Inventor: Gary W. Crook, 2516 Seaboard, Midland, TX (US) 79705

(*) Notice: Subject to any disclaimer, the term of this patent is extended or adjusted under 35 U.S.C. 154(b) by 402 days.

(21) Appl. No.: 10/963,128

(22) Filed: Oct. 12, 2004

(65) Prior Publication Data

US 2006/0082462 A1    Apr. 20, 2006

(51) Int. Cl.
    *G08B 17/10*    (2006.01)
(52) U.S. Cl. .................. 340/632; 340/531; 340/539.11; 340/539.19; 340/539.22; 340/693.5
(58) Field of Classification Search ................. 340/632, 340/531, 539.11, 539.19, 539.22, 693.5; 73/23.5
    See application file for complete search history.

(56) References Cited

U.S. PATENT DOCUMENTS

| | | |
|---|---|---|
| 6,252,510 B1 | 6/2001 | Dungan |
| 6,404,884 B1 * | 6/2002 | Marwell et al. ........ 379/265.13 |
| 6,670,887 B2 | 12/2003 | Dungan |
| 6,794,991 B2 * | 9/2004 | Dungan ..................... 340/632 |
| 7,212,111 B2 * | 5/2007 | Tupler et al. ........... 340/539.18 |
| 2004/0056771 A1 | 3/2004 | Dungan |

* cited by examiner

*Primary Examiner*—Tai T Nguyen
(74) *Attorney, Agent, or Firm*—Robert J. Harter

(57) ABSTRACT

A method allows an H2S alarm system installed at a remote wellsite to be monitored and configured from a distant location. Alert-signals from the alarm system to the distant location and configuration settings from the distant location to the alarm system can be transmitted using the text-messaging feature of a conventional cell phone. The cell phone, for example, can send the H2S alarm system a text message that sets the H2S concentration threshold at which the alarm system triggers an alert. When the H2S concentration reaches the threshold or a fault occurs with the alarm system, the system can send the cell phone a text message that describes the problem, identifies the location of the wellsite, and lists the names and telephone numbers of those that should be notified.

14 Claims, 2 Drawing Sheets

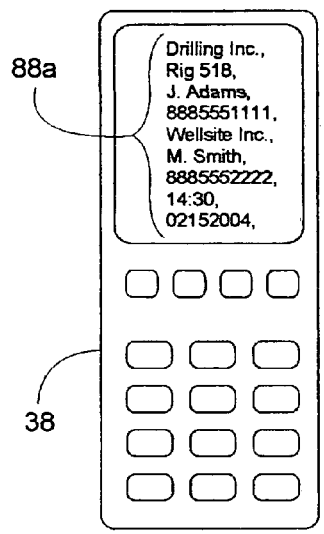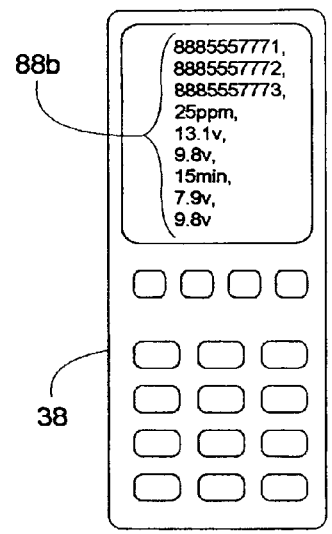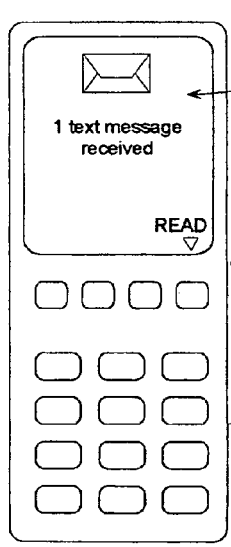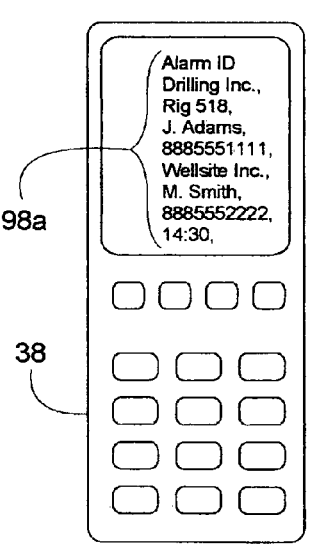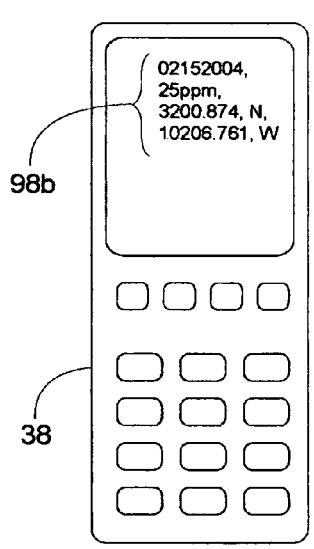

REMOTE CONTROL OF A HYDROGEN SULFIDE GAS ALARM SYSTEM

BACKGROUND OF THE INVENTION

1. Field of the Invention

The subject invention generally pertains to hydrogen sulfide gas alarm systems and more specifically to a method of communicating and remotely configuring such a system.

2. Description of Related Art

Hydrogen sulfide, H2S, is a toxic gas that often accompanies the production of gas, oil and water. H2S can usually be contained, but if it escapes, an H2S monitor can be used for alerting personnel in the area. In response to sensing about 10 to 20 ppm of H2S, typical H2S monitors will sound an alarm that warns of the danger. Once the alarm sounds, personnel often have sufficient time to vacate the area. In some cases, however, someone or everyone in the area may be overcome by the gas and fall to the ground. Since H2S is heavier than air, an unconscious person lying on the ground may continue breathing the toxic gas. If outside help is not quickly summoned to the area, eventually those continuing to breath the gas may die.

U.S. Pat. Nos. 6,252,510 and 6,670,887 and U.S. patent application US-2004/0056771-A1 disclose an H2S system that provides a remote alarm signal upon sensing an excessive amount of H2S at a distant location. The system appears to be designed for an established chemical plant where the H2S monitor is at a fixed, known location. Such a system may be fine for monitoring hydrogen sulfide gas at a particular location, but it may be inadequate in cases where the conditions or location of the H2S monitored area changes from one day to the next.

In the oil and gas industry, for example, on one day, H2S may be monitored at first well site; and on another day, another well site at a completely different location may be monitored. As the location of the worksite changes, other things may also change, such as the expected H2S concentration in the area, the allowable H2S concentration limit for triggering an alarm, parties responsible for the equipment and personnel at the worksite, parties responsible for the worksite itself, the exact location where rescue workers should be sent, etc. Such changes can lead to havoc when an H2S alarm goes off, as there may be little time to react with an appropriate plan of action for the immediate conditions at the site.

Consequently, a need exists for a method of providing a quick and appropriate response to an H2S emergency at remote, spaced-apart worksites where the conditions and location of the worksites may change.

SUMMARY OF THE INVENTION

It is an object of some embodiments to provide a method of configuring and monitoring an H2S alarm system.

It is an object of some embodiments to use the text-messaging feature of a cell phone to remotely communicate with an H2S alarm system.

It is an object of some embodiments is to use the text-messaging feature of a cell phone to remotely configure various settings of an alarm system.

In some embodiments, the H2S alarm setting identifies a service company that is at the worksite.

In some embodiments, the H2S alarm setting identifies a piece of machinery that is at the worksite.

In some embodiments, the H2S alarm setting identifies the name and telephone number of a person representing a service company that is working at the worksite.

In some embodiments, the H2S alarm setting identifies the name of a production company that owns, leases or otherwise possesses the worksite.

In some embodiments, the H2S alarm setting identifies the name and telephone number of a person representing the production company that possesses the worksite.

In some embodiments, the H2S alarm setting includes a series of telephone numbers and an order of sequence for calling those numbers to report a problem that may have occurred at the worksite.

In some embodiments, the H2S alarm setting identifies an H2S concentration threshold for triggering an alert (i.e., either a local alert and/or a call out).

In some embodiments, the H2S alarm setting identifies a voltage limit for a power supply that powers at least part of the H2S alarm system.

In some embodiments, the H2S alarm setting identifies a variable for determining whether the GPS unit is functioning properly.

It is an object of some embodiments is to use the text messaging feature of a cell phone to remotely receive an alert from an H2S alarm system.

In some embodiments, the text message provides information about a problem that has occurred at the worksite.

In some embodiments, the text message identifies a problem with a GPS unit that is associated with the H2S alarm system.

In some embodiments, the text message provides information about a problem pertaining to a power supply that powers at least part of the H2S alarm system.

In some embodiments, the text message identifies the name of a service company that operates machinery at the worksite.

In some embodiments, the text message identifies a particular piece of equipment operating at the worksite.

In some embodiments, the text message identifies the name and telephone number of a person representing a service company that is working at the worksite.

In some embodiments, the text message identifies the name of a production company that owns, leases or otherwise possesses the worksite.

In some embodiments, the text message identifies the name and telephone number of a person representing the production company that possesses the worksite.

In some embodiments, the text message identifies the H2S level that triggered the alert.

In some embodiments, the text message identifies the GPS coordinates of the worksite.

BRIEF DESCRIPTION OF THE DRAWING

FIG. 2 is a front view of a cell phone displaying the first portion of a text message generated by a setting-signal or a confirmation signal.

FIG. 3 is a front view of a cell phone displaying the second portion of a text message generated by a setting-signal or a confirmation signal.

FIG. 4 is a front view of a cell phone displaying the first portion of a text message generated by an alarm-signal.

FIG. 5 is a front view of a cell phone displaying the second portion of a text message generated by an alarm-signal.

FIG. 6 is a front view of a cell phone whose display indicates that the cell phone has received a text message.

DESCRIPTION OF THE PREFERRED EMBODIMENT

Figure 1:
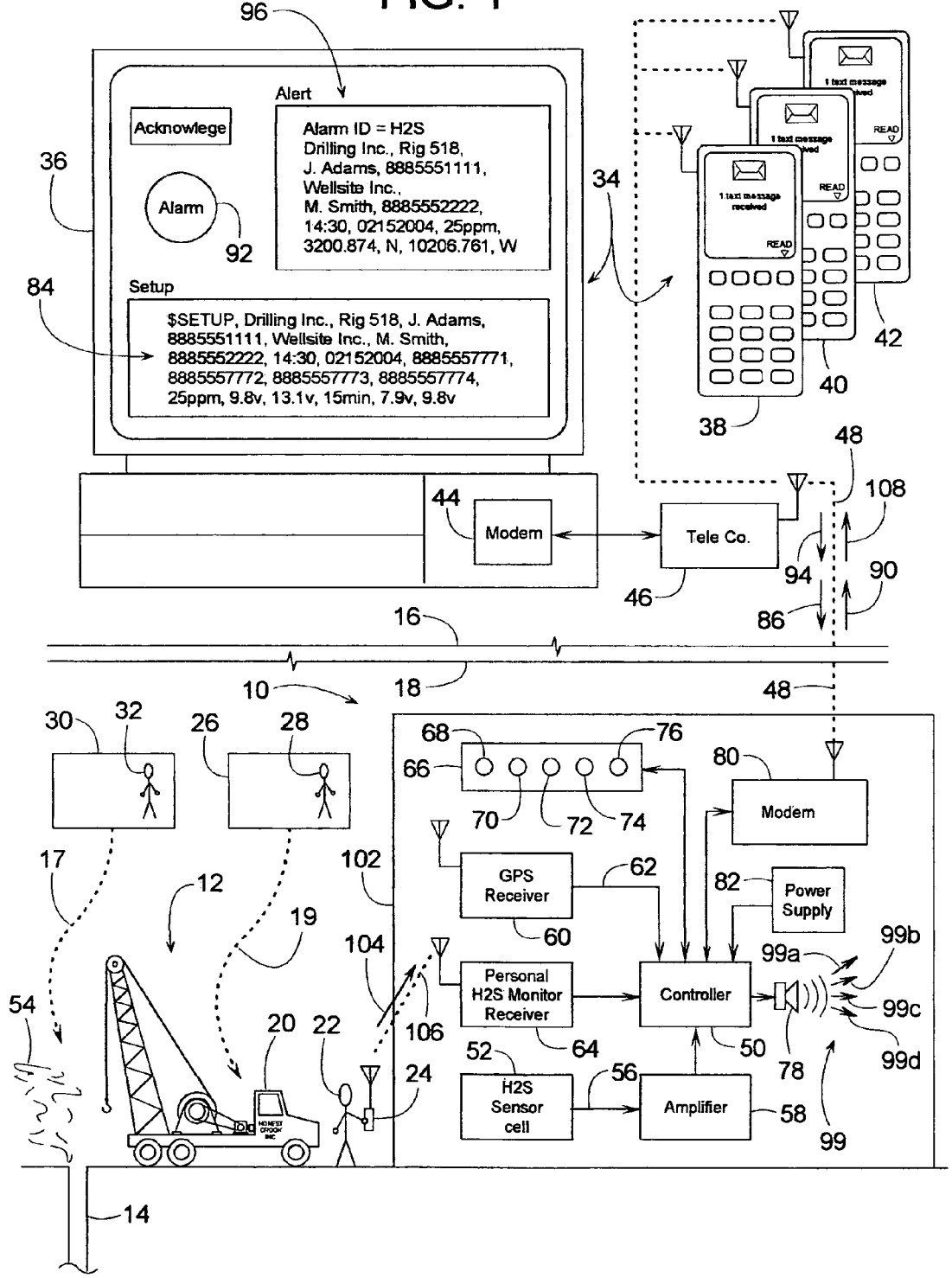
FIG. 1 is a schematic diagram that illustrates a method of remotely configuring and communicating with an H2S alarm system installed at a remote worksite.

FIG. 1 schematically illustrates a method of remotely configuring and communicating with an H2S alarm system 10 used at a worksite. The invention is particularly suited for the oil and gas industry where the worksite is a remote, wide-open outdoor area such as a website 12 that includes a well bore 14. The location of the worksite and the H2S alarm may change from one day to the next. The worksite, for example, may be at one well bore a first day, and the worksite may be at a different well bore at a different remote location on another day.

FIG. 1 shows a pair of broken lines 16 and 18 whose space there between schematically represents a distance of at least five miles to help emphasize the remoteness of website 12. At website 12, or below line 18, there is shown well bore 14, a machine 20 for drilling or servicing the well bore, a worker 22 with an optional personal H2S sensor 24, and H2S alarm system 10. Also shown is a service company 26 that operates machine 20; a person 28 representing service company 26; a production company 30 that owns, leases, operates or otherwise possesses website 14; and a person 32 that represents production company 30. Although companies 26 and 30 and persons 28 and 32 are shown below line 18, broken lines 17 and 19 mean that they are not necessarily physically at website 12.

Several communication units 34 (including units 36, 38, 40, and 42) are shown above line 16, thus units 34 can be, but are not necessarily, at least five miles away from website 12. For illustration purposes, in this particular example, unit 36 is a computer with a modem 44, and units 38, 40 and 42 are portable phones with text messaging capability (i.e., they can send and receive text messages). The term, "portable phone" refers to a handheld unit that includes a small keyboard for directing phone calls and a headset for sending and receiving voice messages. Examples of a portable phone include, but are not limited to, cell phones and satellite phones. Block 46 schematically represents a telephone or communications company that enables units 34 to communicate with alarm system 10 via a wireless communication link 48 made possible by cell phone technology, satellite, radio signals, etc.

Alarm system 10 comprises a programmable controller 50 (e.g., computer, microprocessor, embedded chip, etc.), a conventional H2S sensor cell 52 that senses the concentration of an H2S gas 54 and provides a signal 56 in proportion thereto, a conventional signal amplifier 58 for converting signal 56 to a level that is appropriate for controller 50, a GPS receiver 60 for providing controller 50 with a signal 62 that indicates the global coordinates of website 12, an optional personal H2S monitor receiver 64 (to be explained later), a set of user interfaces 66 (e.g., GPS indicator light 68, alarm status light 70, call-out light 72, confirmation light 74, alarm reset button 76, etc.), a local H2S alarm 78 (e.g., flashing red light and/or audible alarm), a modem 80 for placing controller 50 in communication with remote communication units 34, and a power supply 82 (e.g., one or more batteries for powering items 66, 60, 50, 80 and/or 52).

In operation, production company 30 may request that service company 26 send worker 22 and machine 20 to drill, repair or otherwise service website 12. To protect the safety of worker 22 and others in the area, alarm system 10 is moved to website 12. Alarm system 10 can be reconfigured to suit the situation at any particular website, and this can be done remotely by using computer 36 or portable phones 38, 40 or 42.

One or more settings 84, for instance, can be entered into computer 36, wherein the settings define information relevant to worksite 12. Settings 84 may include contact-related information and/or function-related information. Contact-related information helps identify or helps lead to someone that should be informed or may be able to help should a problem occur at worksite 12. Examples of settings 84 with contact-related information include, but are not limited to, the name of service company 26 (e.g., Drilling Inc.), the name of machine 20 (e.g., Rig 518), the name of person 28 (e.g., J. Adams), that person's telephone number (e.g., 8885551111), the name of company 30 (e.g., Website Inc.), the name of person 32 (e.g., M. Smith), that person's telephone number (e.g., 8885552222), the modem telephone number of computer modem 44 (e.g., 8885557771), the telephone number of cell phone 38 (e.g., 8885557772), the telephone number of cell phone 40 (e.g., 8885557773), and the telephone number of cell phone 42 (e.g., 8885557774).

Function-related information, on the other hand, helps identify or pertains to the operation of alarm system 10. Examples of settings 84 with function-related information include, but are not limited to, an H2S concentration threshold (e.g., 25 ppm) at which point alarm system 10 responds by triggering alarm 78 or calling units 34, one or more allowable voltage limits of power supply 82 (e.g., 9.8v to 13.1v or 7.9v to 9.8v), and a variable for determining whether GPS unit 60 is operational (e.g., the variable could be 15 minutes, wherein a GPS reading would be expected at least once every 15 minutes from a properly operating GPS unit).

Modem 44 can transmit settings 84 from computer 36 to modem 80 of controller 50. Settings 84 are conveyed over wireless communication link 48 and are conveyed as a data stream or a setting-signal depicted by arrow 86.

Alternatively, settings 84 can be entered into portable phone 38, 40 or 42 as a text message 88a and 88b (88a and 88b are actually a single text message that may need one or more pages to display due to the limited size of the phone's display area). Phone 38, for example, can then call modem 84 to deliver text message 88a and 88b (setting-signal 86) to modem 80 of controller 50.

Upon receiving setting-signal 86, in some embodiments, controller 50 and modem 80 may return a confirmation-signal 90 to the sender of setting-signal 86, whereby confirmation-signal 90 confirms that alarm system 10 has actually received setting-signal 86. Confirmation-signal 86 may simply be another text message that resembles text message 88a/88b of FIGS. 2 and 3.

Settings 84 are stored on a memory associated with controller 50. Some items of settings 84 determine how alarm system 10 responds to problems pertaining to website 12 or problems with alarm system 10 itself, and other items of settings 84 provide valuable information that can assist others in responding to such problems.

Examples of problems that may trigger alarm system 10 to call for help (i.e., send an alarm-signal 108 include, but are not limited to, the concentration H2S exceeding 25 ppm or some other threshold defined by settings 84, the supply voltage of controller 50 going beyond 9.8-13.1v or some other voltage range defined by settings 84, the supply voltage of H2S sensor cell 52 going beyond 7.9-9.8v or some other voltage range defined by settings 84, and/or GPS unit 60 failing to provide a global coordinates reading at least once every 15 minutes or some other period defined by settings 84.

Upon detecting such problems, controller 50 uses modem 80 to notify units 34 by calling them simultaneously or sequentially (e.g., minutes apart). The order in which they are called may be the same order of sequence that the various phone numbers are listed in FIGS. 1 and 3. Mouse-clicking on an acknowledge button 92 enables computer 36 to respond to the problem by sending an acknowledgement signal 94 to controller 50, which in turn illuminates confirmation indicator light 74 for those at the website to see. Acknowledge button 92 terminates the repeated sequential calling of units 34.

In calling out, controller 50 and modem 80 provide units 34 with a text message such as text message 96 of FIG. 1 or text message 98a and 98b of FIGS. 4 and 5. Text message 98a/98b is sent via alarm-signal 108 that wireless communication link 48 transmits from modem 80 to modem 44 and/or to cell phones 38, 40 and/or 42. Before actually being able to view the text message, the cell phones may first display a notice 100, as shown in FIG. 6, that a text message has been sent. Text message 98a and 98b are actually a single text message that may need one or more pages to display due to the limited size of the cell phone's display area.

The text message 96 or 98a/98b provides an "Alarm ID" that indicates the nature of the problem, such as an H2S triggered alarm, GPS failure, supply voltage problem, etc. In addition, text message 96 or 98a/98b may also provide helpful information such as the name of service company 26 (e.g., Drilling Inc.), the name of machine 20 (e.g., Rig 518), the name of person 28 (e.g., J. Adams), that person's telephone number (e.g., 8885551111), the name of company 30 (e.g., Website Inc.), the name of person 32 (e.g., M. Smith), that person's telephone number (e.g., 8885552222), the current time of day (e.g., 14:30 or 2:30 p.m.), the current date (e.g., 02152004 or Feb. 15, 2004), an H2S concentration value that triggered the callout, the wellsite's GPS coordinates (e.g., 3200.874-North, 10206.761-West).

In some embodiments, alarm 82 of system 10 may be triggered by H2S sensor cell 52 and/or by the optional personal H2S sensor 24 that is carried or worn by worker 22. H2S sensor cell 52 may be contained or mounted to an enclosure 102 that houses controller 50 and/or other components of alarm system 10. In response to H2S sensor 52, controller 50 may activate the local alarm 78 when the concentration of H2S reaches a first threshold, such as 10 ppm, and may further callout an alarm alert when the concentration reaches a higher predefined threshold, such as 25 ppm.

Alternatively, or in addition to H2S sensor 52, personal H2S monitor receiver 24 may notify controller 50 that an excessive H2S concentration exists as sensed by personal H2S alarm 24 (which also includes an H2S sensor cell). Upon sensing an unacceptable concentration of H2S, personal H2S alarm 24 transmits an alarm signal 104 to receiver 64 via a wireless communication link 106.

In some embodiments, the local alarm 78 provides various audible and/or visual alarm signals 99 that are distinguishable from one another to communicate different messages to the workers at worksite 12. Alarm signals 99 may be distinguishable by some sound characteristic such as the pitch, volume, and/or pattern of the sound (pulsating, wave shape, etc.).

In same cases, a first alarm signal 99a may be an early warning red light that shines when the H2S concentration reaches a first threshold of e.g., 15 ppm, and a second alarm signal 99b may be an audible alarm that sounds when the concentration reaches a second threshold of e.g., 20 ppm. Second alarm signal 99b may also be a warning that H2S alarm system 10 is about make one or more phone calls to summon help from one or more locations that are remote relative to worksite 12 (e.g., summon help from someone tending one of units 34). Second alarm signal 99b may sound for a predetermined period (e.g., one minute) to give worker 22 time to manually reset alarm system 10 via reset button 76, whereby reset button 76 terminates second alarm 108b and prevents alarm system 10 from sending alarm-signal 108.

If alarm system 10 is not reset within the allowable period, then a third alarm signal 99c may sound, which could notify worker 22 and others at worksite 12 that alarm system 10 is calling for outside help. A fourth alarm signal 99d may sound in response to acknowledgement signal 94, thereby notifying the workers at worksite 12 that someone remote relative to worksite 12 has acknowledged receiving alarm-signal 108.

Using distinguishable alarm signals 99 for communicating different messages to worker 22 and others at worksite 12 can be quite valuable. If there are only four workers at the worksite, for instance, and two are unconscious for having been overcome by H2S gas, alarm signals 99 notify the other two conscious workers that alarm system 10 will summon additional help. This allows both conscious workers to "air-up" (put on an air tank) so that one conscious worker can enter the H2S contaminated area to rescue the two unconscious workers while the other conscious worker oversees the rescue. Without alarm signals 99, one of the conscious workers would need to call for outside help, which would make it unsafe for the other conscious worker to make an unsupervised rescue attempt alone.

In some embodiments, GPS unit 60 is a GARMIN Mini 25-HVS; modem 80 is a Data Remote CD9020 Global star Qualcomm GSP1620; controller 4 is a PK2500 controller provided by Z-World, Inc. of Davis, Calif.; and H2S sensor cell 52 is an Electro-Chem. H2S sensor cell. Personal H2S alarm 24 and receiver 64 may include conventional transmitter/receiver circuitry for placing the two in wireless communication with each other.

Although the invention is described with reference to a preferred embodiment, it should be appreciated by those of ordinary skill in the art that other variations are well within the scope of the invention. The Internet, for example, may be used to facilitate the communication of signal 86, 90, 94, and/or 108 between alarm system 10 and communication units 34. Therefore, the scope of the invention is to be determined by reference to the following claims.

the invention claimed is:

1. A method of configuring an H2S alarm system for a worksite, comprising:
   installing the H2S alarm system at the worksite; and
   transmitting a setting-signal via a wireless communication link from a communication unit to the H2S alarm system, wherein the setting-signal provides a contact-related information.

2. The method of claim 1, wherein the contact-related information identifies a service company that possesses a machine that is disposed at the worksite.

3. The method of claim 1, wherein the contact-related information identifies a machine disposed at the worksite.

4. The method of claim 1, wherein a machine possessed by a service company is disposed at the worksite, and the contact-related information identifies a person representing the service company.

5. The method of claim 1, wherein a machine possessed by a service company is disposed at the worksite, and the contact-related information identifies a telephone number of a person representing the service company.

6. The method of claim 1, wherein the contact-related information identifies a production company that possesses the worksite.

7. The method of claim 1, wherein the contact-related information identifies a person representing a production company that possesses the worksite.

8. The method of claim 1, wherein a production company possesses the worksite, and the contact-related information identifies a telephone number of a person representing the production company.

9. The method of claim 1, wherein the contact-related information includes a plurality of telephone numbers and an order of sequence for calling the plurality of telephone numbers.

10. The method of claim 1, wherein the communication unit is a portable phone.

11. The method of claim 10, wherein the portable phone is a cell phone.

12. The method of claim 10, wherein the portable phone is a satellite phone.

13. The method of claim 1, wherein the communication unit is a computer with a modem.

14. The method of claim 1, further comprising transmitting a confirmation-signal from the H2S alarm system to the communication unit, wherein the confirmation-signal indicates that the alarm system has received the setting-signal.

* * * * *